United States Patent
Dillon et al.

(10) Patent No.: US 9,157,733 B2
(45) Date of Patent: Oct. 13, 2015

(54) METHOD OF DATA ACQUISITION FOR THREE-DIMENSIONAL IMAGING

(75) Inventors: Robert F. Dillon, Bedford, NH (US); Andrew F. Vesper, Townsend, MA (US); Timothy I. Fillion, Bedford, MA (US)

(73) Assignee: Dimensional Photonics International, Inc., Wilmington, MA (US)

( * ) Notice: Subject to any disclaimer, the term of this patent is extended or adjusted under 35 U.S.C. 154(b) by 513 days.

(21) Appl. No.: 13/217,595

(22) Filed: Aug. 25, 2011

(65) Prior Publication Data

US 2012/0062701 A1 Mar. 15, 2012

Related U.S. Application Data

(60) Provisional application No. 61/381,731, filed on Sep. 10, 2010.

(51) Int. Cl.
*H04N 13/00* (2006.01)
*A61C 3/00* (2006.01)
*G01B 11/24* (2006.01)
*A61B 5/00* (2006.01)
*A61B 5/107* (2006.01)
(Continued)

(52) U.S. Cl.
CPC .............. *G01B 11/24* (2013.01); *A61B 5/0062* (2013.01); *A61B 5/0088* (2013.01); *A61B 5/1077* (2013.01); *A61C 9/006* (2013.01); *G01B 11/25* (2013.01); *G01B 11/2527* (2013.01)

(58) Field of Classification Search
CPC ... A61B 5/0062; A61B 5/0088; A61B 5/1077
See application file for complete search history.

(56) References Cited

U.S. PATENT DOCUMENTS

| 5,545,039 A | 8/1996 | Mushabac |
| 5,870,191 A | 2/1999 | Shirley et al. |

(Continued)

FOREIGN PATENT DOCUMENTS

| JP | 2008194108 | 8/2008 |
| JP | 2009078133 | 4/2009 |

(Continued)

OTHER PUBLICATIONS

European Search Report in counterpart European patent application No. 11 179 796.5 dated Dec. 29, 2011, Munich; 7 pages.

(Continued)

*Primary Examiner* — Chikaodili E Anyikire
*Assistant Examiner* — Md Haque
(74) *Attorney, Agent, or Firm* — Schmeiser, Olsen & Watts LLP; William G. Guerin (57) ABSTRACT

Described are embodiments of methods of obtaining three-dimensional (3D) surface data of an object scene such as an intra-oral cavity. For example, measured surfaces may include the enamel surface of teeth, the dentin substructure of teeth, gum tissue and various dental structures. The methods can also be applied in medical applications and other applications in which 3D measurement data are acquired with maneuverable 3D measurement devices. In certain embodiments, the measurement device is positioned and translated to enable 3D data to be acquired for a backbone 3D data set. Subsequent controlled motion of the measurement device enables additional 3D data to be acquired and accurately joined to the backbone 3D data set.

23 Claims, 6 Drawing Sheets (51) Int. Cl.
*A61C 9/00* (2006.01)
*G01B 11/25* (2006.01)

(56) References Cited

U.S. PATENT DOCUMENTS

| | | | |
|---|---|---|---|
| 6,217,334 | B1 | 4/2001 | Hultgren |
| 6,648,640 | B2 * | 11/2003 | Rubbert et al. ............. 433/24 |
| 6,993,177 | B1 * | 1/2006 | Bachelder .................. 382/151 |
| 7,286,954 | B2 * | 10/2007 | Kopelman et al. ........... 702/152 |
| 7,494,338 | B2 * | 2/2009 | Durbin et al. ................ 433/29 |
| 2002/0064752 | A1 | 5/2002 | Durbin et al. |
| 2003/0049585 | A1 | 3/2003 | Severance |
| 2006/0154198 | A1 * | 7/2006 | Durbin et al. ................ 433/29 |
| 2010/0290060 | A1 * | 11/2010 | Mohazzab et al. .......... 356/492 |
| 2011/0090513 | A1 | 4/2011 | Seidl et al. |

FOREIGN PATENT DOCUMENTS

| | | |
|---|---|---|
| WO | 2007030340 A1 | 3/2007 |
| WO | 2009085752 A2 | 7/2009 |

OTHER PUBLICATIONS

Office Action in related Japanese patent application No. 2011-195641, mailed on May 14, 2013; 3 pages.
First Office Action in related Chinese patent application No. 201110273932.X, mailed on Dec. 23, 2013; 24 pages.
Second Office Action in related Chinese Patent Application No. 201110273932.X, mailed on Aug. 27, 2014; 5 pages.

* cited by examiner

METHOD OF DATA ACQUISITION FOR THREE-DIMENSIONAL IMAGING

RELATED APPLICATION

This application claims the benefit of the earlier filing date of U.S. Provisional Patent Application Ser. No. 61/381,731, filed Sep. 10, 2010 and titled "Method of Data Processing and Display for a Three-Dimensional Intra-Oral Scanner," the entirety of which is incorporated herein by reference.

FIELD OF THE INVENTION

The invention relates generally to three-dimensional (3D) imaging of the intra-oral cavity. More particularly, the invention relates to a method of acquiring 3D image data of an object scene using a plurality of 3D measurement scans and generating a complete 3D image from the scans.

BACKGROUND

In a typical dental or medical 3D camera or scanner imaging system, a series of two-dimensional (2D) intensity images of one or more object surfaces in an object scene is acquired where the illumination for each image may vary. In some systems, structured light patterns are projected onto the surface and detected in each 2D intensity image. For example, the projected light pattern can be generated by projecting a pair of coherent optical beams onto the object surface and the resulting fringe pattern varied between successive 2D images. Alternatively, the projected light pattern may be a series of projected parallel lines generated using an intensity mask and the projected pattern shifted in position between successive 2D images. In still other types of 3D imaging systems, techniques such as confocal imaging are employed.

In a dynamic 3D imaging system, a series of 3D data sets is acquired while the camera or scanner is in motion relative to the object scene. For example, the imaging system can be a wand or other handheld device that a user manually positions relative to the object scene. In some applications, multiple objects surfaces are measured by moving the device relative to the objects so that surfaces obscured from view of the device in one position are observable by the device in another position. For example, in dental applications the presence of teeth or other dental features in a static view can obscure the view of other teeth. A processing unit registers the overlapped region of all acquired 3D data to obtain a full 3D data set representation of all surfaces observed during the measurement procedure.

SUMMARY

In one aspect, the invention features a method of obtaining 3D surface data for an object scene. A 3D imaging device is positioned so that a measurement field of view includes a first portion of a directional view of an object scene at a starting point in the object scene and to acquire 3D data for the measurement field of view. The 3D imaging device is translated while maintaining the directional view of the object scene so that the measurement field of view translates across a remainder of the directional view of the object scene. During translation, the 3D imaging device acquires 3D data for the translated measurement field of view that are registered with the 3D data for the starting point in the object scene. The 3D data for the positioned and translated measurement field of views define a backbone 3D data set. The 3D imaging device is positioned so that the measurement field of view includes a second portion of the directional view of the object scene and the 3D imaging device acquires 3D data for the measurement field of view that overlap a portion of the backbone 3D data set. The 3D data that overlap the portion of the backbone 3D data set are joined to the backbone 3D data set. The 3D imaging device is maneuvered so that the measurement field of view includes a portion of an orthogonal directional view of the object scene and the 3D imaging device acquires 3D data for the measurement field of view that are registered to the backbone 3D data set.

In another aspect, the invention features a method of obtaining 3D surface data of a dental arch. A 3D measurement device is positioned so that a structured light pattern generated by the 3D measurement device illuminates a portion of an occlusal surface of a dental arch at a first starting point. 3D data are acquired for the illuminated portion of the occlusal surface. The 3D measurement device is translated so that the structured light pattern illuminates a remainder of the occlusal surface of the dental arch. 3D data are acquired for the remainder of the occlusal surface and registered to the 3D data for the portion of the occlusal surface. The 3D data for the portion and the remainder of the occlusal surface define a backbone 3D data set for the dental arch. The 3D measurement device is positioned so that the structured light pattern illuminates a portion of the occlusal surface of the dental arch to thereby acquire 3D data that overlap a portion of the backbone 3D data set. The 3D data that overlap a portion of the backbone 3D data set are joined to the backbone 3D data set. The 3D measurement device is rotated so that the structured light pattern is incident on one of a portion of a buccal surface or a portion of a lingual surface of the dental arch to thereby acquire 3D data for the portion of the buccal or lingual surface that are registered to the backbone 3D data set.

In still another aspect the invention features a method of obtaining 3D surface data for an intra-oral cavity. A 3D measurement device is positioned in an intra-oral cavity so that a measurement field of view of the 3D measurement device includes a portion of an occlusal surface of a dental arch at a starting point and 3D data are acquired for the measurement field of view. The 3D measurement device is translated so that the measurement field of view includes a remainder of the occlusal surface of the dental arch. 3D data acquired for the translating measurement field of view are registered to the 3D data for the portion of the occlusal surface. The 3D data for the portion and for the remainder of the occlusal surface define a backbone 3D data set for the dental arch. The 3D measurement device is positioned so that the measurement field of view includes a portion of the occlusal surface to thereby acquire 3D data that overlap a portion of the backbone 3D data set. The 3D data that overlap a portion of the backbone 3D data set are joined to the backbone 3D data set. The 3D measurement device is moved so that the measurement field of view includes a portion of the intra-oral cavity that is separate from the occlusal surface of the dental arch to thereby acquire 3D data for the portion of the intra-oral cavity that are registered to the backbone 3D data set.

BRIEF DESCRIPTION OF THE DRAWINGS

The above and further advantages of this invention may be better understood by referring to the following description in conjunction with the accompanying drawings, in which like numerals indicate like structural elements and features in the various figures. For clarity, not every element may be labeled in every figure. The drawings are not necessarily to scale, emphasis instead being placed upon illustrating the principles of the invention.

DETAILED DESCRIPTION

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill in the art having access to the teaching herein will recognize additional implementations, modifications and embodiments, as well as other fields of use, which are within the scope of the present disclosure as described herein.

The methods of the present invention may include any of the described embodiments or combinations of the described embodiments in an operable manner. In brief overview, embodiments of the methods of the invention enable an accurate 3D measurement of one or more object surfaces. In various embodiments described below, the methods relate to the acquisition of 3D data during a 3D measurement procedure. The methods are described with respect to measurements of an oral cavity, such as a measurement made by a clinician in a dental application in which measured surfaces may include the enamel surface of teeth, the dentin substructure of teeth, gum tissue and various dental structures (e.g., posts, inserts and fillings). It will be appreciated that the methods can also be applied in medical applications and other applications in which 3D measurement data are acquired with 3D scanning devices under direct manipulation by an operator or otherwise maneuvered by a control system.

In the embodiments described below, 3D measurement systems use structured illumination patterns generated by interferometric fringe projection or other techniques. Imaging components acquire 2D images used to determine positional information of points on the surface of objects based on the structured illumination of the objects.

U.S. Pat. No. 5,870,191, incorporated herein by reference, describes a technique referred to as Accordion Fringe Interferometry (AFI) that can be used for high precision 3D measurements based on interferometric fringe projection. AFI-based 3D measurement systems typically employ two closely-spaced coherent optical sources to project the interferometric fringe pattern onto the surface of the object. Images of the fringe pattern are acquired for at least three spatial phases of the fringe pattern.

Figure 1:
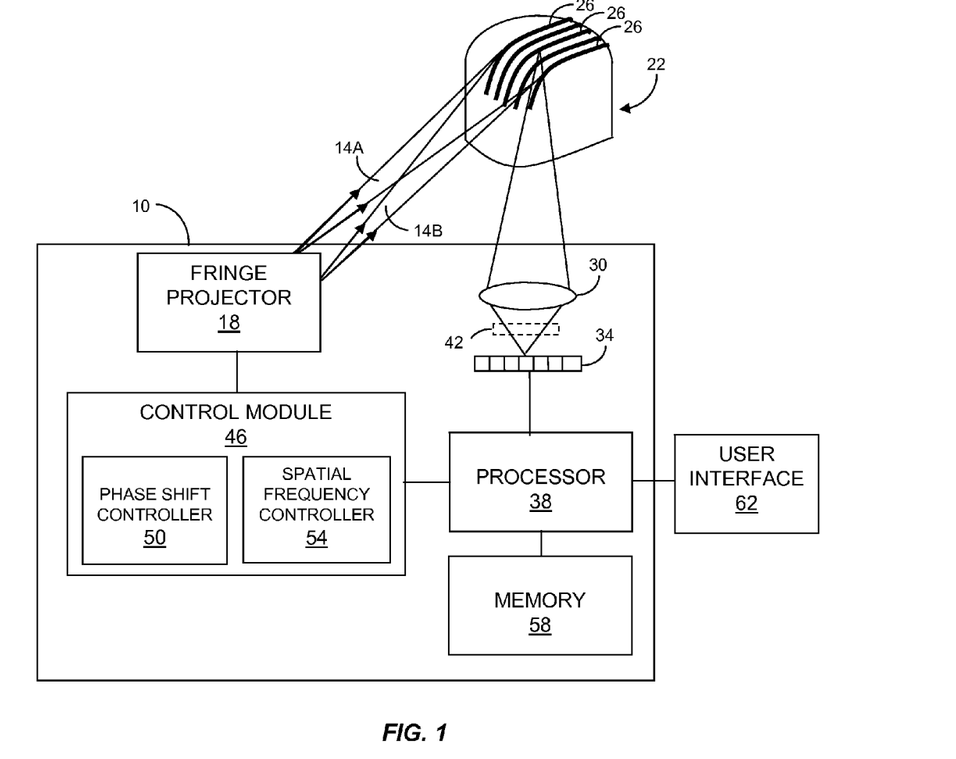
FIG. 1 is a block diagram showing an example of a measurement system that can be used to obtain a 3D image of an object scene.

FIG. 1 illustrates an AFI-based 3D measurement system 10 used to obtain 3D images of one or more objects 22. Two coherent optical beams 14A and 14B generated by a fringe projector 18 are used to illuminate the surface of the object 22 with a pattern of interference fringes 26. An image of the fringe pattern at the object 22 is formed by an imaging system or lens 30 onto an imager that includes an array of photodetectors 34. For example, the detector array 34 can be a two-dimensional charge coupled device (CCD) imaging array. An output signal generated by the detector array 34 is provided to a processor 38. The output signal includes information on the intensity of the light received at each photodetector in the array 34. An optional polarizer 42 is oriented to coincide with the main polarization component of the scattered light. A control module 46 controls parameters of the two coherent optical beams 14 emitted from the fringe projector 18. The control module 46 includes a phase shift controller 50 to adjust the phase difference of the two beams 14 and a spatial frequency controller 54 to adjust the pitch, or separation, of the interference fringes 26 at the object 22.

The spatial frequency of the fringe pattern is determined by the separation of two virtual sources of coherent optical radiation in the fringe projector 18, the distance from the virtual sources to the object 22, and the wavelength of the radiation. The virtual sources are points from which optical radiation appears to originate although the actual sources of the optical radiation may be located elsewhere. The processor 38 and control module 46 communicate to coordinate the processing of signals from the photodetector array 34 with respect to changes in phase difference and spatial frequency, and the processor 38 determines 3D information for the object surface according to the fringe pattern images.

The processor 38 calculates the distance from the imaging system 30 and detector array 34 to the object surface for each pixel based on the intensity values for the pixel in the series of 2D images generated after successive phase shifts of the fringe patterns. Thus the processor creates a set of 3D coordinates that can be displayed as a point cloud or a surface map that represents the object surface. The processor 38 communicates with a memory module 58 for storage of 3D data generated during a measurement procedure. A user interface 62 includes an input device and a display to enable an operator such as a clinician to provide operator commands and to observe the acquired 3D information in a near real-time manner. For example, the operator can observe a display of the growth of a graphical representation of the point cloud or surface map as different regions of the surface of the object 22 are measured and additional 3D measurement data are acquired.

Figure 2:
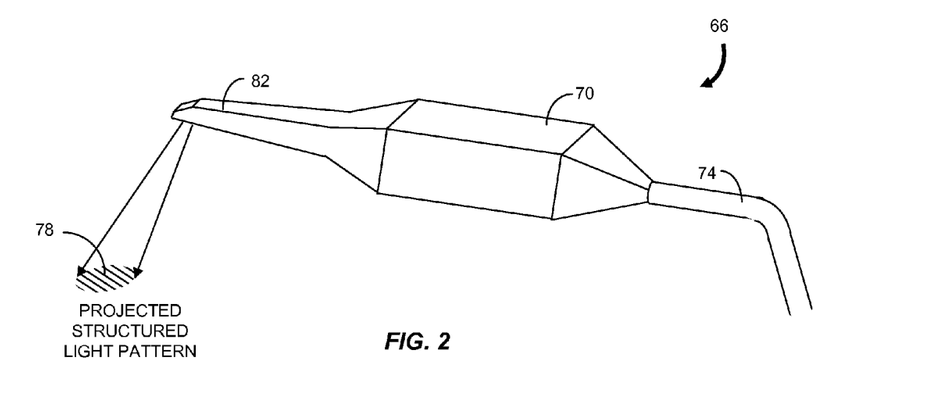
FIG. 2 illustrates a maneuverable wand that is part of a 3D measurement system used to obtain 3D measurement data for an intra-oral cavity.

FIG. 2 illustrates a handheld 3D measurement device in the form of a maneuverable wand 66 that can be used to obtain 3D measurement data for an intra-oral cavity. The wand 66 includes a body section 70 that is coupled through a flexible cable 74 to a processor and other system components (not shown). The wand 66 generates a structured light pattern 78 that is projected from near the projection end 82 to illuminate a surface to be measured. For example, the structured light pattern 78 can be an interferometric fringe pattern based on the principles of an AFI measurement system as described above for FIG. 1. The wand 66 can be used to obtain 3D data for a portion of a dental arch. The wand 66 is maneuvered within the intra-oral cavity by a clinician so that 3D data are obtained for all surfaces that can be illuminated by the structured light pattern 78.

Figure 3:
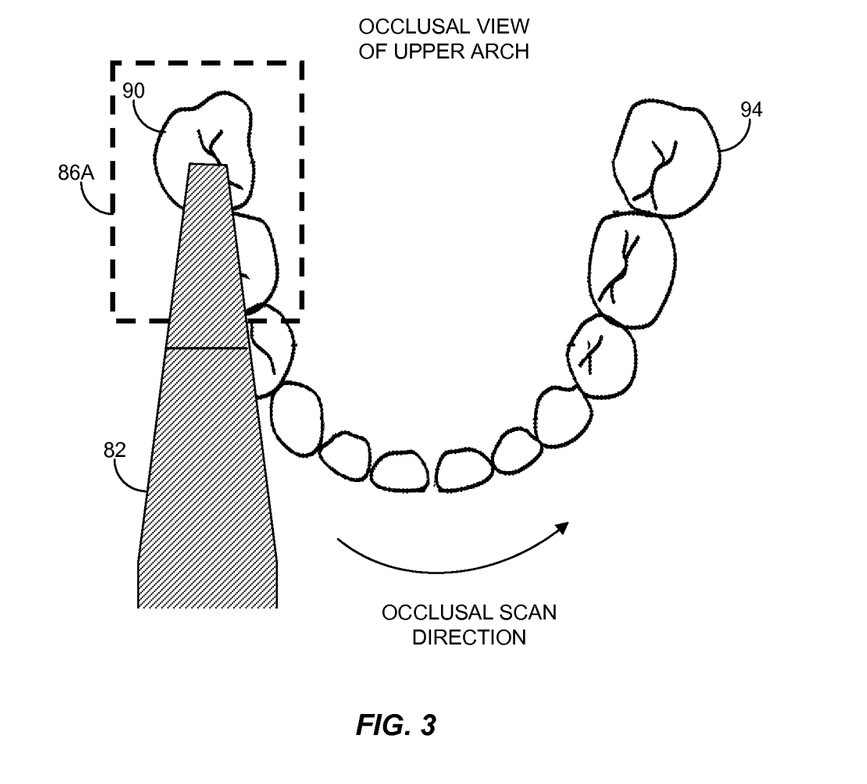
FIG. 3 illustrates how an upper dental arch is measured using a handheld 3D measurement device such as the maneuverable wand of FIG. 2.
Figure 4:
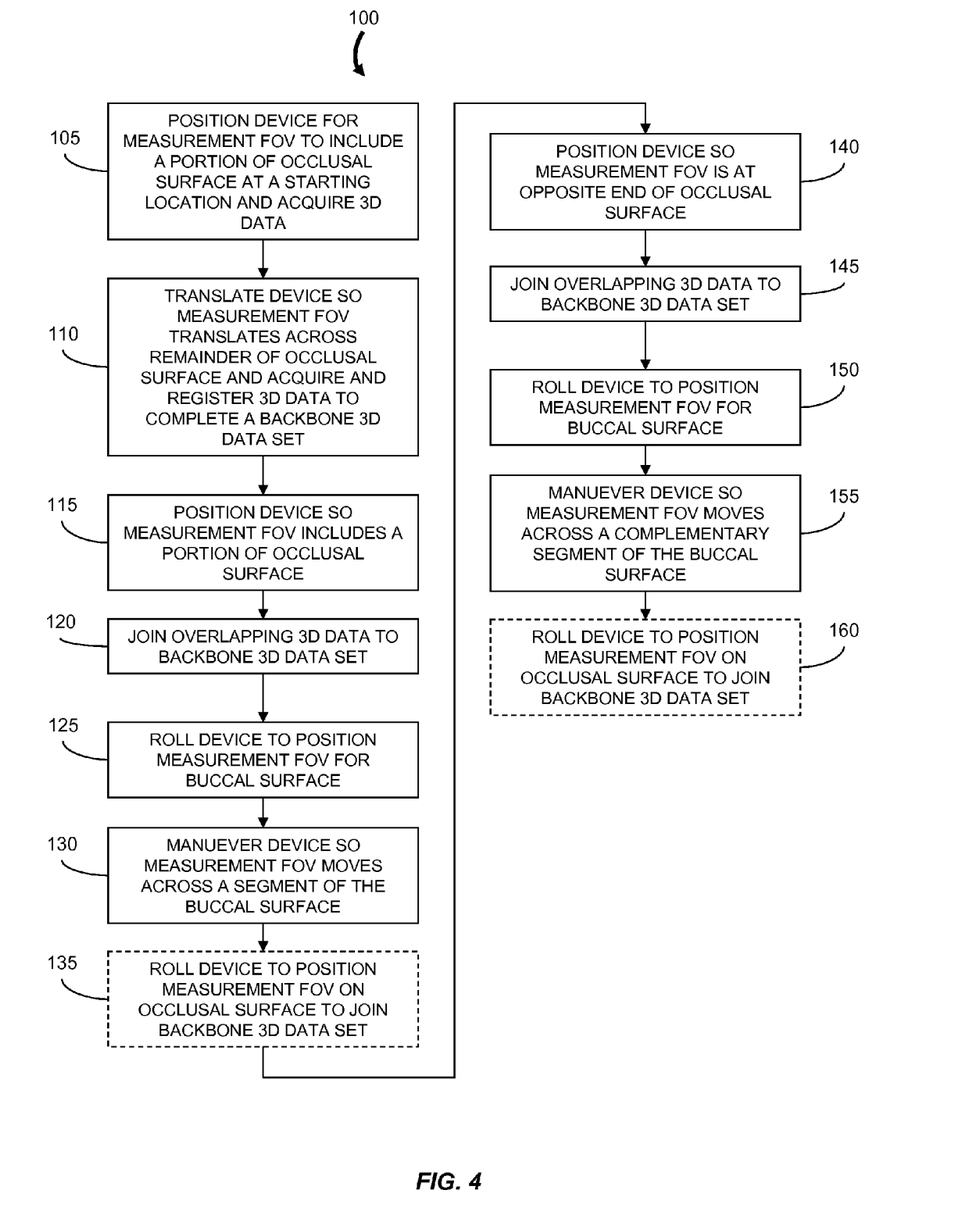
FIG. 4 a flowchart representation of an embodiment of a method of obtaining 3D surface data for a dental arch according to the invention.

FIG. 3 illustrates an intra-oral application in which an upper dental arch is measured using a handheld 3D measurement device such as the wand 66 of FIG. 2. Reference is also made to FIG. 4 which presents a flowchart representation of an embodiment of a method 100 of obtaining 3D surface data for a dental arch. The measurement results in a complete 3D data set that accurately represents the full arch of a patient, i.e., from the back molar on one side of the arch to the back molar on the opposite side of the arch. During data processing, stitching errors and motion-induced errors can degrade the measurement results. For a 3D measurement device that includes a 2D imager with a small measurement field of view (FOV) (e.g., 13 mm×10 mm) relative to the full arch, hundreds of 3D data sets may be stitched together to obtain the complete 3D data set for the arch.

According to the method 100, numerous overlapping 3D data sets are stitched together in a common coordinate reference. The 3D data are obtained in a preferred manner or sequence so that the "final" 3D data set resulting from all the 3D data more accurately represents the dental arch. In particular, a backbone 3D data set is first generated and additional sequences of 3D data are subsequently joined to the backbone 3D data set. Individual scan segments are used to acquire subsets of 3D data for the final point cloud. Limited motion of the wand during the 3D data acquisition for each scan segment results in reduced measurement error and increased measurement accuracy.

Figure 5:
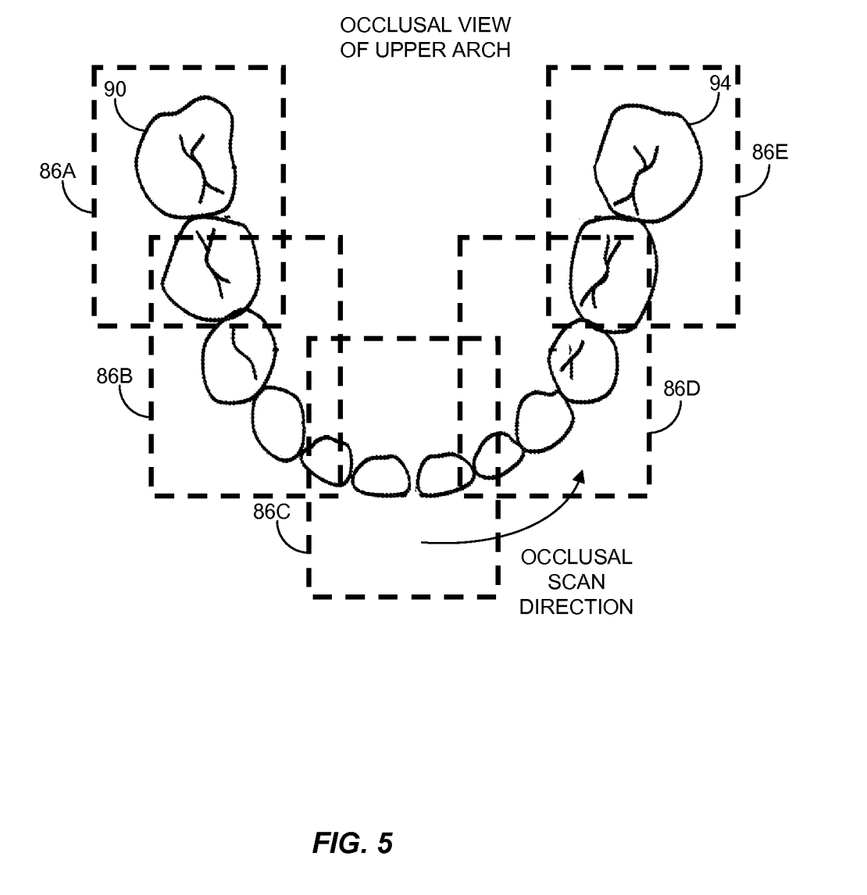
FIG. 5 shows a measurement field of view at five different positions along an upper dental arch during 3D data acquisition for an occlusal scan according to the method of FIG. 4.

A clinician performs the 3D measurement method 100 by positioning (step 105) the wand so that the structured light pattern illuminates a portion of an occlusal surface of the dental arch at a starting location, for example, at one end of the dental arch. 3D data are acquired for the illuminated portion of the occlusal surface. In this example, data acquisition starts by acquiring data from within a measurement field of view 86A at the patient's left back molar 90 of the upper dental arch as shown in FIG. 3. The wand is then moved (step 110) from the patient's left back molar 90 along the arch to the right back molar while maintaining a substantially occlusal view. FIG. 5 shows the measurement field of view 86A to 86E for several positions (five positions A to E) along the arch. The full occlusal scan does not require significant rotation of the wand during this portion of the 3D measurement procedure. Rotation and focus induced errors are therefore reduced in comparison to scans obtained by manipulating the wand for other views of the arch. In some embodiments, the motion of the wand is substantially in a direction parallel to the stripes or fringes of the structured light pattern. The primary motion of the wand during the occlusal scan is restricted substantially to a single plane. Advantageously, the occlusal view includes features having substantially higher spatial frequency content than other views. That is, the occlusal view more readily shows rapidly varying structure (e.g., gaps between teeth) that improve the accuracy for stitching of 3D data relative to other scan views (i.e., buccal and lingual). Thus the 3D data corresponding to the occlusal scan defines a backbone that can be used for attachment by other 3D data sets obtained during other directional scan views as necessary to obtain a complete set of 3D data for the arch.

Figure 6A:
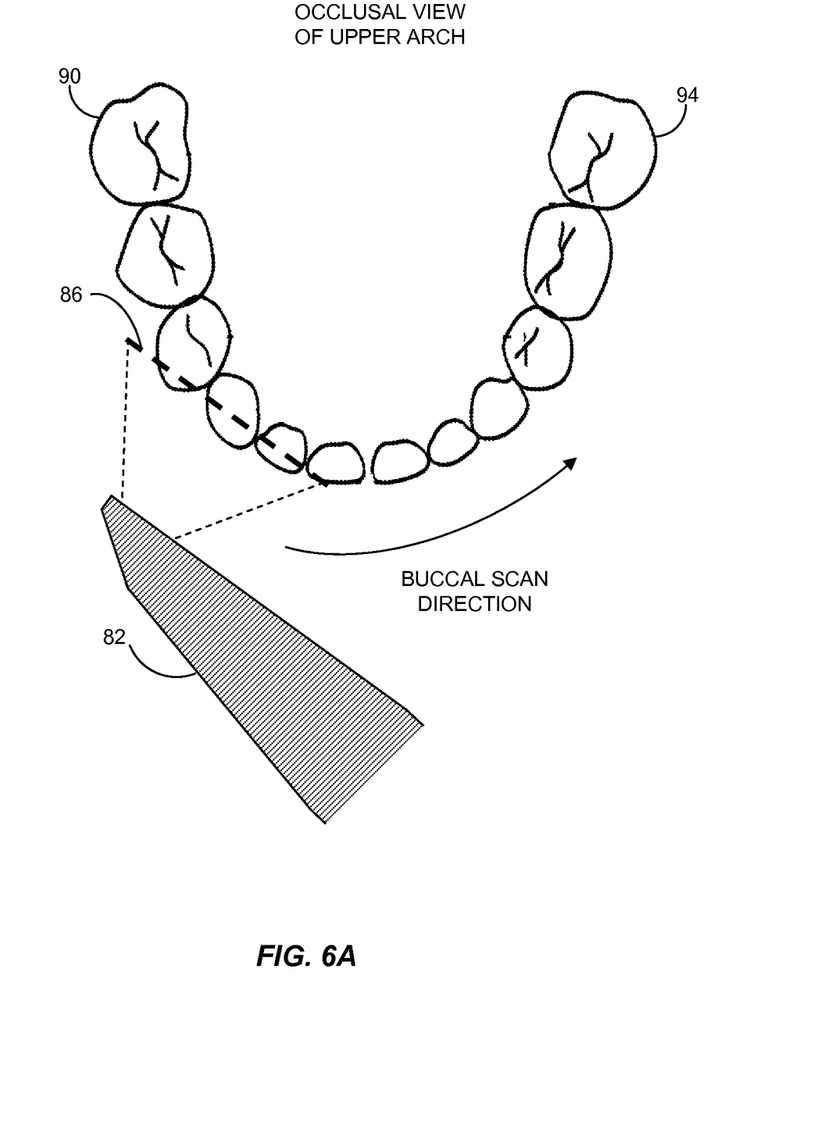
FIG. 6A and FIG. 6B are an occlusal view and a buccal view, respectively, of a wand and the corresponding location of the measurement field of view during a scan segment of a buccal surface.
Figure 6B:
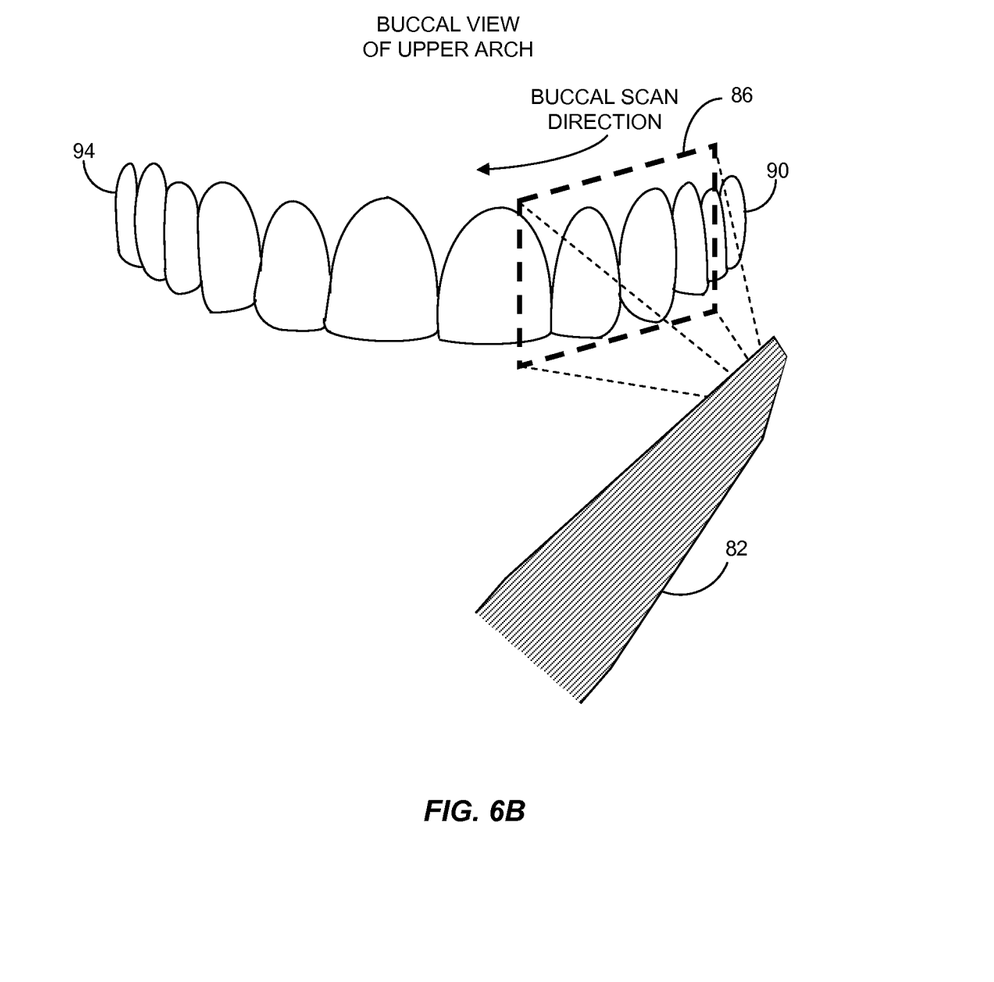

To continue the measurement procedure, the clinician positions (step 115) the wand so that the structured light pattern illuminates a portion of the occlusal surface, for example, near or at one end of the arch, and 3D data are acquired that overlap a portion of the backbone 3D data set. Preferably, the 3D measurement system provides an affirmative visual or audible indication to the clinician when the new 3D data for the real-time position of the structured light pattern "locks on" to the display of a point cloud for the backbone 3D data set. The newly-acquired 3D data are then registered or joined (step 120) to the backbone 3D data and serve as the start of a buccal scan segment for the arch. The wand is then rotated about its primary axis and moved (step 125) so that a portion of the buccal surface of the arch is illuminated with the structured light pattern and 3D data are acquired. The wand is then maneuvered (step 130) by the clinician so that the structured light pattern moves along a segment of the buccal surface. For example, the wand may be moved so that the structured light pattern is scanned in time from the patient's back left molars to just beyond the midpoint of the buccal surface. FIG. 6A and FIG. 6B show an occlusal view and a buccal view, respectively, of the position of the projection end 82 of the wand and the corresponding location of the measurement field of view (and structured light pattern) part way through this scan segment of the buccal surface. Optionally, the clinician can rotate (step 135) the wand so that the structured light pattern illuminates the midpoint of the occlusal surface. In this manner, the structured light pattern is used to acquire 3D data in an occlusal view that overlay data in the backbone 3D data set to more accurately "register" to the existing 3D data in the common coordinate reference system.

A complementary buccal scan segment can now be performed. The clinician positions (step 140) the wand so that the structured light pattern illuminates a portion of the occlusal surface at the opposite end of the arch and 3D data are acquired that overlap a portion of the backbone 3D data set. The 3D data at this location are joined (step 145) to the 3D backbone data set and serve as the start of a complementary buccal scan segment for the arch. The wand is then rotated about its primary axis (step 150) so that a portion of remainder of the buccal surface of the arch is illuminated with the structured light pattern and 3D data are acquired. Subsequently, the wand is maneuvered (step 155) by the clinician so that the structured light pattern moves along the remainder of the buccal surface segment. For example, the wand may be moved so that the structured light pattern is moved in time from the patient's back right molars to just beyond the midpoint of the buccal surface. Optionally, the clinician can rotate (step 160) the wand so that the structured light pattern illuminates the midpoint region of the occlusal surface and 3D data are acquired in an occlusal view that overlay the data in the backbone 3D data set. Thus the 3D data for this buccal segment are accurately registered in the common reference system of the backbone 3D data set.

To complete the 3D measurement of the arch, the clinician obtains 3D data for the lingual surface of the dental arch in a manner similar to that used for obtaining 3D data for the buccal surface. More specifically, steps 125 to steps 160 are performed by replacing all references to the buccal surface with references to the lingual surface. In total, five scan segments are performed to obtain a full set of 3D data for the final 3D data set for the dental arch.

In effect, the steps of joining 3D data to the backbone 3D data set allows sequences of individual 3D images to be attached by referring to a subset of the chronologically ordered 3D images in the backbone 3D data set. This joining technique "primes the stitcher" so that the subsequent scan is properly registered to the backbone 3D data set and accurately shares the same global coordinate system.

In an alternative embodiment, the order of scan segments can differ. For example, acquisition of the 3D data for the two lingual segments can precede acquisition of the 3D data for the buccal segments.

In other embodiments, the clinician can use a greater number of buccal and lingual scan segments and the extent of each segment can be smaller. In such embodiments, the measurement system displays various portions of the backbone 3D data set to allow joining the backbone 3D data set at other locations.

In the embodiments described above for the method 100, the structured light pattern and measurement field of view used for 3D data acquisition are moved along various surfaces of a dental arch and repositioned by manipulating the position and rotation of a wand. The method can be adapted for other types of 3D measurement systems. For example, the method can be performed using a measurement field of view of a wand or maneuverable 3D measurement device that can be translated, rotated and positioned in a similar manner to the structured light pattern such that 3D data initially generated during the procedure can be used to generate a backbone 3D data set and subsequent 3D data can be joined to the backbone 3D data set to obtain a high accuracy 3D data representation of an object scene. Furthermore, the method preferably obtains 3D measurement data first for a directional view that substantially requires only two dimensional translation of the measurement field of view and in which high spatial frequency content is observable to create the backbone 3D data set and subsequent directional views are used to generate additional 3D data that can be attached to the backbone 3D data set.

While the invention has been shown and described with reference to specific embodiments, it should be understood by those skilled in the art that various changes in form and detail may be made therein without departing from the spirit and scope of the invention as recited in the accompanying claims.

What is claimed is:

1. A method of obtaining three-dimensional (3D) surface data of an object scene, the method comprising:
    positioning a 3D imaging device so that a measurement field of view includes a portion of a directional view of an object scene and to acquire 3D data for the measurement field of view at a start of a first scan segment;
    translating the 3D imaging device while maintaining the directional view of the object scene so that the measurement field of view translates across a remainder of the directional view of the object scene during the first scan segment and the 3D imaging device acquires 3D data for the translated measurement field of view that are registered with the 3D data for the start of the first scan segment, the 3D data acquired during the first scan segment defining a backbone 3D data set;
    positioning the 3D imaging device so that the measurement field of view includes a portion of the directional view of the object scene for which 3D data were previously acquired during the first scan segment so that the 3D imaging device acquires 3D data for the measurement field of view that overlap a portion of the backbone 3D data set;
    joining the 3D data that overlap the portion of the backbone 3D data set to the backbone 3D data set for a start of a second scan segment; and
    maneuvering the 3D imaging device while continuing to acquire 3D data during the second scan segment so that the measurement field of view includes a portion of an orthogonal directional view of the object scene so that the 3D data for the measurement field of view that are acquired during the maneuvering of the 3D imaging device are registered to the backbone 3D data set.

2. The method of claim 1 further comprising maneuvering the 3D imaging device during the second scan segment so that the measurement field of view scans across a segment of the orthogonal directional view of the object scene and the 3D imaging device acquires 3D data for the measurement field of view that are registered to the backbone 3D data set.

3. The method of claim 1 further comprising displaying the acquired 3D data for observation.

4. The method of claim 3 wherein the acquired 3D data are displayed as a 3D point cloud.

5. The method of claim 3 wherein the acquired 3D data are displayed as one or more object surfaces.

6. The method of claim 3 wherein positioning the 3D imaging device so that the measurement field of view includes a portion of the directional view of the object scene for which 3D data were previously acquired during the first scan segment comprises overlaying a two-dimensional image of the measurement field of view to a display of the backbone 3D data set.

7. The method of claim 1 wherein the object scene comprises at least a portion of an intra-oral cavity.

8. The method of claim 1 wherein the object scene comprises a dental arch.

9. A method of obtaining three-dimensional (3D) surface data of a dental arch, the method comprising:
    positioning a 3D measurement device such that a structured light pattern generated by the 3D measurement device illuminates a portion of an occlusal surface of a dental arch and 3D data are acquired for the illuminated portion of the occlusal surface at a start of a first scan segment;
    translating the 3D measurement device during the first scan segment so that the structured light pattern illuminates a remainder of the occlusal surface of the dental arch and 3D data are acquired for the remainder of the occlusal surface that are registered to the 3D data for the portion of the occlusal surface, the 3D data for the first scan segment defining a backbone 3D data set for the dental arch;
    positioning the 3D measurement device so that the structured light pattern illuminates a portion of the occlusal surface of the dental arch for which 3D data were previously acquired during the first scan segment to thereby acquire 3D data that overlap a portion of the backbone 3D data set;
    joining the 3D data that overlap a portion of the backbone 3D data set to the backbone 3D data set for a start of a second scan segment; and
    rotating the 3D measurement device while continuing to acquire 3D data during the second scan segment so that the structured light pattern is incident on one of a portion of a buccal surface or a portion of a lingual surface of the dental arch to thereby acquire 3D data for the portion of the buccal or lingual surface that are registered to the backbone 3D data set.

10. The method of claim 9 wherein an angular orientation of the 3D measurement device is substantially unchanged during the translation of the 3D measurement device.

11. The method of claim 9 further comprising displaying the acquired 3D data for observation.

12. The method of claim 11 wherein the acquired 3D data are displayed as a 3D point cloud.

13. The method of claim 11 wherein the acquired 3D data are displayed as one or more object surfaces.

14. The method of claim 9 further comprising moving the 3D measurement device so that the projection of the structured light pattern is moved across a first segment of the buccal or lingual surface to thereby acquire 3D data for the second scan segment.

15. The method of claim 14 further comprising:
positioning the 3D measurement device so that the projection of the structured light pattern is incident on a portion of the occlusal surface for which 3D data were previously acquired during the first scan segment to thereby acquire 3D data that overlap another portion of the backbone 3D data set;
joining the 3D data that overlap the another portion of the backbone 3D data set to the backbone 3D data set for a start of a third scan segment;
rotating the 3D measurement device while continuing to acquire 3D data during the third scan segment so that the projection of the structured light pattern is incident on another portion of the buccal surface or the lingual surface of the dental arch to thereby acquire 3D data for the another portion of the buccal or lingual surface; and
moving the 3D measurement device so that the projection of the structured light pattern is moved across a second segment of the buccal or lingual surface to thereby acquire 3D data for the third scan segment.

16. The method of claim 14 further comprising rotating the 3D measurement device while continuing to acquire 3D data during the second scan segment so that the projection of the structured light pattern is incident on a portion of the occlusal surface to thereby acquire 3D data that overlap the backbone 3D data set.

17. The method of claim 15 further comprising rotating the 3D measurement device while continuing to acquire 3D data during the third scan segment so that the projection of the structured light pattern is incident on a portion of the occlusal surface to thereby acquire 3D data that overlap the backbone 3D data set.

18. The method of claim 9 wherein positioning the 3D measurement device so that the projection of the structured light pattern is incident on a portion of the occlusal surface of the dental arch for which 3D data were previously acquired during the first scan segment comprises overlaying a two-dimensional image of the portion of the occlusal surface illuminated by the structured light pattern onto a graphical display of the backbone 3D data set.

19. The method of claim 9 wherein the structured light pattern comprises a striped pattern.

20. The method of claim 9 wherein the structured light pattern is an interferometric intensity pattern.

21. The method of claim 9 wherein the 3D measurement device does not rotate during the translation of the projection of the structured light pattern across the remainder of the occlusal surface of the dental arch.

22. The method of claim 9 wherein the 3D measurement device is a handheld 3D scanner.

23. A method of obtaining three-dimensional (3D) surface data of an intra-oral cavity, the method comprising:
positioning a 3D measurement device in an intra-oral cavity so that a measurement field of view of the 3D measurement device includes a portion of an occlusal surface of a dental arch and acquiring 3D data for the measurement field of view at a start of a first scan segment;
translating the 3D measurement device during the first scan segment so that the measurement field of view includes a remainder of the occlusal surface of the dental arch and 3D data acquired for the translating measurement field of view are registered to the 3D data for the portion of the occlusal surface, the 3D data for the first scan segment defining a backbone 3D data set for the dental arch;
positioning the 3D measurement device so that the measurement field of view includes a portion of the occlusal surface for which 3D data were previously acquired during the first scan segment to thereby acquire 3D data that overlap a portion of the backbone 3D data set;
joining the 3D data that overlap a portion of the backbone 3D data set to the backbone 3D data set for a start of a second scan segment; and
moving the 3D measurement device while continuing to acquire 3D data during the second scan segment so that the measurement field of view includes a portion of the intra-oral cavity that is separate from the occlusal surface of the dental arch to thereby acquire 3D data for the portion of the intra-oral cavity that are registered to the backbone 3D data set.

* * * * *